(12) United States Patent
Wacey

(10) Patent No.: US 12,320,717 B2
(45) Date of Patent: Jun. 3, 2025

(54) MONITORING SYSTEM

(71) Applicant: EtherSec Industries Ltd, London (GB)

(72) Inventor: Adam Wacey, London (GB)

(73) Assignee: EtherSec Industries Ltd, London (GB)

( * ) Notice: Subject to any disclaimer, the term of this patent is extended or adjusted under 35 U.S.C. 154(b) by 139 days.

(21) Appl. No.: 18/273,764

(22) PCT Filed: Jan. 24, 2022

(86) PCT No.: PCT/EP2022/051457
§ 371 (c)(1),
(2) Date: Jul. 22, 2023

(87) PCT Pub. No.: WO2022/161903
PCT Pub. Date: Aug. 4, 2022

(65) Prior Publication Data
US 2024/0087324 A1    Mar. 14, 2024

(30) Foreign Application Priority Data

Jan. 26, 2021 (GB) .................................... 2101023

(51) Int. Cl.
*G01L 1/22* (2006.01)
*G06V 10/141* (2022.01)
(Continued)

(52) U.S. Cl.
CPC .............. *G01L 1/22* (2013.01); *G06V 10/141* (2022.01); *G06V 10/143* (2022.01); *G06V 20/52* (2022.01);
(Continued)

(58) Field of Classification Search
CPC ........ G06V 20/52; G06V 20/40; H04N 23/73; H04N 7/181; H04W 12/06
See application file for complete search history.

(56) References Cited

U.S. PATENT DOCUMENTS

| 10,250,948 B1 | 4/2019 | Bortz et al. |
| 2002/0126005 A1 | 9/2002 | Hardman et al. |

(Continued)

FOREIGN PATENT DOCUMENTS

| CN | 111933297 A | 11/2020 |
| WO | 2011154949 A2 | 12/2011 |

(Continued)

OTHER PUBLICATIONS

Adam Wacey, "Monitoring System," co-pending U.S. Appl. No. 18/273,763, national phase entry of PCT/EP2022/051449.
(Continued)

*Primary Examiner* — Girumsew Wendmagegn
(74) *Attorney, Agent, or Firm* — Smartpat PLC

(57) ABSTRACT

An exposure monitoring system is disclosed. The system comprises: at least one camera to observe a monitoring area; a plurality of beacons each comprising at least one light emitting element and a controller to provide an actuation sequence to the light emitting element; and a video analytics system. The video analytics system comprises a processor configured to receive video data captured by the at least one camera, analyse the video for the presence of light emissions from the beacons, decode the actuation sequence of the light emissions from any detected beacon to provide an identification for the beacon, compile a location history for each beacon, over time, detected within the surveillance area, and determine an exposure risk associated with each beacon. A method of exposure monitoring is also disclosed.

18 Claims, 7 Drawing Sheets

(51) Int. Cl.
*G06V 10/143* (2022.01)
*G06V 20/52* (2022.01)
*G06V 30/19* (2022.01)
*G08B 21/02* (2006.01)
*H05K 1/02* (2006.01)

(52) U.S. Cl.
CPC ....... *G06V 30/19007* (2022.01); *G08B 21/02* (2013.01); *H05K 1/028* (2013.01); *H05K 2201/10151* (2013.01)

(56) References Cited

U.S. PATENT DOCUMENTS

| | | |
|---|---|---|
| 2007/0205791 A1 | 9/2007 | Ahmad et al. |
| 2011/0128384 A1 | 6/2011 | Tiscareno et al. |
| 2011/0247863 A1 | 10/2011 | Watanabe |
| 2016/0050750 A1 | 2/2016 | Rogers et al. |
| 2018/0143313 A1* | 5/2018 | Wetzler .................. G01S 5/163 |
| 2018/0146545 A1 | 5/2018 | Wang et al. |
| 2018/0357380 A1 | 12/2018 | Wang et al. |
| 2019/0215063 A1 | 7/2019 | Darabi |
| 2020/0176125 A1 | 6/2020 | Chatterjea et al. |
| 2021/0112657 A1 | 4/2021 | Edmundson et al. |
| 2021/0318191 A1 | 10/2021 | Okulov |
| 2023/0136688 A1 | 5/2023 | Leerentveld |

FOREIGN PATENT DOCUMENTS

| | | |
|---|---|---|
| WO | 2016128967 A1 | 8/2016 |
| WO | 2019038271 A1 | 2/2019 |

OTHER PUBLICATIONS

Fraenkel, Aviezri S., and Shmuel T. Kleinb. "Robust universal complete codes for transmission and compression." Discrete Applied Mathematics 64, No. 1 (1996): 31-55.

Nguyen, Cong T., Yuris Mulya Saputra, Nguyen Van Huynh, Ngoc-Tan Nguyen, Tran Viet Khoa, Bui Minh Tuan, Diep N. Nguyen et al. "A comprehensive survey of enabling and emerging technologies for social distancing—Part I: Fundamentals and enabling technologies." Ieee Access 8 (2020): 153479-153507.

* cited by examiner

MONITORING SYSTEM

FIELD OF INVENTION

The invention relates to a system and methods of monitoring. Particularly to systems and methods of exposure monitoring.

BACKGROUND

It is often desirable to monitor or measure the exposure to a risk of one or more subjects, operating within a hazardous environment. One such example, can be found, in subjects working with radioactive sources—radiographers operating x-ray machines, scientists working with radioactive material or operatives in a nuclear power station—are all provided with wearable, radioactivity monitoring badges. By measuring the degree of risk (for example, the degree of radiation exposure), mitigating measures can be taken against these risks, such as limiting a subject's time in the risk environment, once a certain radiation dose has been adsorbed over a specific time period.

Risks inherent in other environments may prove harder to empirically measure. For example, the exposure to a vector of infectious diseases such as SARS-CoV-2 causing COVID-19, cannot be directly measured in real time. However, this does not prevent a risk exposure and monitoring approach being operationally useful, since proxies for exposure to the infectious vector can be employed. Indeed, such an approach could prove critically important in protecting front-line medical or care staff, for whom some level of viral exposure may be almost unavoidable. As such, it would be advantageous to provide a system which can monitor risk, for example, by automatically tracking contact time and distance between subjects within an area.

Various technologies could be used for monitoring and tracking subjects or contacts and the data yielded by these technologies subsequently used for risk monitoring. For example, contact tracing applications have been developed that are typically based on Bluetooth communication technology using conventional mobile devices. Likewise, RFID based technologies can be used in more dedicated tracking systems. Unfortunately, such radio-based technologies may not be suitable for use in all environments. For example, technology may be incompatible with PPE (personal protection equipment) or may be undesirable or prohibited from some environments due to presence of delicate equipment sensitive to RF frequencies. For example, hospitals (and particularly intensive care units thereof) may have highly sensitive medical devices which need protection from RF radiation. Indeed, as Lieshout et al, have demonstrated, "RFID caused interference in 34 of the 123 tests they performed" and "could shut down equipment patients rely on".

It will be appreciated that there is a desire to provide risk monitoring methods and systems which can overcome one or more of the disadvantages of the systems described above. In particular it would be desirable to provide a monitoring system which operates passively and/or automatically such that it does not interfere with or distract subjects. It would also be desirable to provide risk monitoring systems and methods which are able to monitor even high sensitivity areas (such as Intensive Care Unit's) without any danger of impendence to sensitive equipment operating in the area.

SUMMARY OF INVENTION

In accordance with a first aspect of the invention, there is provided an exposure monitoring system comprising: at least one camera to observe a monitoring area; a plurality of beacons each comprising at least one light emitting element and a controller to provide an actuation sequence to the light emitting element; and a video analytics system. The video analytics system comprises a processor configured to receive video data captured by the at least one camera, analyse the video for the presence of light emissions from the beacons, decode the actuation sequence of the light emissions from any detected beacon to provide an identification for the beacon, compile a location history for each beacon, over time, detected within the surveillance area, and determine an exposure risk associated with each beacon.

The actuation signal may be configured to cause the light emitting element to emit a binary signal comprising sequential on/off pulses.

Advantageously, by using a light emitting beacon in conjunction with video analytics ingesting feeds from a camera, embodiments of the invention avoid the use of radio-frequency based sources and are thus deployable in almost any environment. Embodiments of the invention may, for example, be implemented using a conventional (or even, already in-situ) CCTV camera system, to enable installation with minimal disruption to the monitoring area. It will be appreciated that this may be particularly important in situations such as during an epidemic when medical facilities are under high demand and cannot, therefore, be set aside for the installation of new, complex and/or dedicated equipment.

A video surveillance system with identifiable beacons has, for example, been proposed in the applicants co-pending patent application GB1916245.2 (filed 8 Nov. 2019) and the skilled person will appreciate that features of the system disclosed therein could be used in implementing embodiments of the present invention. In particular the system of GB1916245.2 introduces a secure verification of the beacon identity without the need for any additional systems. Such an arrangement could be used in embodiments of the present invention to provide increased reliability and security.

It may be appreciated that systems in accordance with the invention could compile a beacon location history over an ongoing time period (for example maintaining data over a rolling period). Other embodiments could have a pre-defined (and optionally configurable) time period which could for example correspond to a time period such as a day or week or a working shift pattern.

The processor may be configured to use the location history of each beacon to determine proximity to at least one exposure source. The proximity may be used in calculating the exposure risk. The proximity may be determined with respect to time. For example, a combination record of distance and time could be accumulated, or the proximity could be divided into proximity bands or zones with the time within each recorded and/or accumulated.

The exposure source may be a fixed point defined within or relative to the monitoring area. For example, the exposure source could be defined as an article of equipment or a region of a room. Further, another subject bearing the wearable may also act as a source of exposure to the infectious vector and this example is known to hold true in the case the disease COVID-19

The exposure source may be at least one of the plurality of beacons. For example, a beacon could be attached to an exposure source. A dedicated risk beacon could be used in some embodiments. However, to provide maximum system flexibility it may be possible to designate any beacon suitable for use with the system as being an exposure source.

In some embodiments the processor may determines a potential relative exposure risk for each beacon detected within the field relative to any other beacons detected within the field. The processor may comprise a machine-readable storage and may use the storage to maintain a database of relative exposure risk for the plurality of beacons. The database may for example store a record or history of proximity and temporal data. Advantageously, determining a potential relative risk between separate beacons (even when those beacons have not been identified as a source of risk) may enable risks to be determined if a beacon is later identified as a potential source. This may, for example, apply with infectious diseases where subjects are monitored by beacons and one subject is subsequently found to be infected. Accordingly, the video analytics system may have an input for flagging a specific beacon identification as an exposure source. In response to a new input the processor uses the potential relative exposure to determine a revised exposure risk for each beacon.

At least some beacons may be configured as a wearable device. For example, a beacon may be provided in a badge or lanyard.

The light emitting element may emit infrared spectrum light, for example the light emitting element may be one or more infrared LEDs.

The processor comprises a machine-readable storage comprising a database of unique identification keys for a plurality of beacons.

The controller uses an encoding algorithm to provide a non-repeating actuation sequence and the processor uses the encoding algorithm in identifying the beacon. A video surveillance system with identifiable beacons has, for example, been proposed in the applicants co-pending patent application GB1916245.2 (filed 8 Nov. 2019) and the skilled person may appreciate that features of the system disclosed therein could be used in implementing embodiments of the present invention. In particular the system of GB1916245.2 introduces a secure verification of the beacon identity without the need for any additional systems. Such an arrangement could be used in embodiments of the present invention to provide increased reliability and security.

The exposure monitoring system may be a medical monitoring system, for example an infectious disease exposure monitoring system. The monitoring area may for example be a treatment area for infectious diseases. The exposure source may be a known carrier of an infectious disease. The processor may, for example be configured to estimate risk based upon viral exposure due to proximity and time relative to any known infected subjects. The beacons may be configured to be worn by medical personal.

According to a further aspect of the invention there is provided a method of monitoring exposure, the method comprising: providing at least one camera to capture video of a surveillance field; providing at least one subject within the surveillance field with a beacon to transmit an encoded light sequence; analysing video from the at least one camera to: detect the beacon output within the surveillance field, decode the light sequence from the beacon to identify the beacon, track the location of the beacon over time, and determine the exposure risk to the subject based upon the location of the beacon over time.

It will be appreciated that features described above with respect to system embodiments may also be applicable to embodiments of the method.

Determining the exposure risk comprises determining the proximity, and associated duration, of the subject to an exposure source.

The exposure source may be identified by a beacon. The method may further comprise flagging at least one subject with a beacon as an exposure source.

The method may further comprise determining and storing the relative proximity over time when multiple beacons are identified within the surveillance field.

The method of monitoring exposure may be a method of monitoring medical exposure, for example exposure to an infectious disease. The method may comprise identifying at least one carrier of an infectious disease. The method may identify and track beacons to determine the risk of a subject associated with the beacon having been exposed to an infectious disease.

In some embodiments the exposure monitoring system or method of monitoring exposure may be used for infectious disease analysis. For example, the exposure risk information generated by the system or method may be stored and subsequently compared to actual disease contraction records. Such historical analysis may be used for research purposes (for example identifying how safety procedures can be refined) or to provide machine learning to improve future exposure risk determination in methods and systems according to embodiments.

In some embodiments the exposure monitoring system or method of monitoring exposure may be used as a bridge between theoretical and empirical infectious disease analysis. For example, multiple theoretical mathematical models of transmission for COVID-19 have been constructed analysing factors such as proximity, dwell time, temperature, humidity, and the flow of air within an environment. The data collected by the exposure monitoring system is very fine grained and an example of empirical data, which can be fed into the theoretical mathematical models, serving to validate the efficacy of these models.

In some embodiments the exposure monitoring system or method of monitoring exposure may be used for infectious disease analysis in real time. Upon exceeding a risk threshold the subject of that risk may then be alerted to their dangerous exposure so that they may mitigate their further risk accumulation. The notification may be attempted automatically by the exposure monitoring system using electronic means such as sending email or alerting the subject by sending a notification to their mobile device.

The beacon(s) in embodiments of the invention may use any convenient light emitting element and the selection may depend upon environmental factors (for example the range of detection required in a particular application or ambient lighting conditions). However, in some embodiments the light emitting element may emit light from the non-visible spectra. References herein to non-visible spectra light may be understood to refer to electro-magnetic spectra which falls outside of the portion which is normally visible to the human eye (which may, for example, be wavelengths between approximately 380 to 740 nm). Infrared light emitted from a source, such as an infrared LED is, for example, generally considered non-visible light, even though some secondary wavelengths emitted by the LED may be observable as a dull red glow to the human eye. In embodiments, the camera may comprise a sensor for detecting non-visible spectra light. The use of non-visible light is advantageous, in ensuring that the beacon is not distracting or a nuisance. Further, a non-visible light beacon may be preferable for security purposes, since the coded actuation sequence of the beacon is concealed from normal human observation.

The non-visible light employed may be of an infrared wavelength. As such, the light emitting element may emit light in the infrared spectrum. For example, one wavelength of the infrared spectrum may be at or around 850 nm. The camera may include a sensor that is attuned to be sensitive to light transmitted at a wavelengths of 850 nm. Advantageously, camera equipment which can detect 850 nm wavelength Infrared is readily commercially available since "commercial of the shelf" CCTV cameras use LED's at this wavelength as floodlights ("often called black light in marketing material"), to covertly illuminate low light scenes. If it is desirable to further reduce the visibility of the beacon to the human eye, light emissions of a lower wavelength (such as 920 nm range) could be utilised. It will however be appreciated that photons of such a lower wavelengths have less power and therefore provide less illumination.

The system may comprise a plurality of beacons, for example, for attachment or use by a plurality of persons or objects. In such embodiments the controller of each beacon may provide a distinct coded actuation sequence. For example, the controller may allow one of a predetermined plurality of coded actuation sequences to be selected, for example, during an initial configuration or updating of the beacon. Alternatively, the controller of each beacon may be pre-programmed with a uniquely coded actuation sequence. The processor of the analytics system may can access a machine-readable storage comprising a database of unique identification keys for a plurality of beacons.

Each beacon may have a uniquely coded actuation sequence (as a series of on/off flashes of the light emitting element) to enable identification by the video analytics system. In some embodiments the controller may be provided with an encoding algorithm to provide a changing actuation sequence. The video analytics system processor may use the same encoding algorithm, and which may be compared to the actuation sequence to verify the identity of the beacon. An advantage of using an encoding algorithm may be that it prevents simple "cloning" by observation of the output from a beacon and copying this to a new device. Changing actuation sequences for use in such embodiments are known for example from authentication systems used for generating one-time passwords or pass-codes.

In some embodiments the controller may use the encoding algorithm to derive an actuation sequence based upon an identification key and a sequence-based value. For example, the sequence-based value may be generated by a counter or use a pre-determined number sequence. The processor verifies the identification key using a current sequence value (for example the processor may have a corresponding counter or stored pre-determined number sequence).

In some embodiments the controller may use the encoding algorithm to derive an actuation sequence based upon an identification key and a time-based value. For example, the controller may further comprise a clock. The processor may verify the identification key using a current time value. The processor may therefore include a clock which may for example be synchronised with the controller.

The video surveillance system of some embodiments may comprise at least, a first camera to observe a first monitoring zone and at least a second camera to observe a second monitoring zone. The processor may be further configured to use the verified identity of the beacon to track movement over time through the first and second surveillance fields. Thus, some embodiments may advantageously provide a system which is able to track movement of a single subject from camera to camera across a time period and monitoring zones. Further embodiments could be arranged to carry out such multi-camera tracking even in a crowded environment in which several beacons are present by verifying the individual beacon identities.

The beacon may comprise a plurality of light emitting elements. The actuation sequence of each light emitting element may be synchronised. For example, the light emitting elements may each light simultaneously in accordance with the coded actuation sequence (such that the elements are effectively acting as a combined light source). In some embodiments the synchronisation of the light emitting elements may use one or more elements as individual light sources in providing a coded actuation sequence (for example a row of elements could be utilised together to provide a number of "bits" when activated).

When a beacon includes a plurality of light emitting elements this may also provide further advantages to the system. For example, multiple elements may have different positions or orientations to increase detectability by the video camera. If at least two of a plurality of light emitting elements are spaced apart by a known spacing distance the processor of the video analytics system may be configured to derive a depth location of the beacon within images from the video data using the spacing distance of the light emitting elements in the video data. In some examples a single beacon could include light emitting elements with a set spacing or alternatively multiple beacons could be placed on a subject or object at a set spacing apart.

Whilst embodiments of the invention could be implemented on a local area network basis (and indeed, for high security environments, an air-gapped network may be a preferred configuration), typically greater flexibility may be achieved by configuring a system in accordance with embodiments to operate over a wider network. For example, the system according to some embodiments, may further comprises a network for receiving video output from the at least one camera and transmitting video data to the video analytics system. The video analytics system could, therefore, be remotely located relative to the monitored area. For example, a cloud-based system could be provided, in which a single centralised video analytics system could be employed, consuming video data from a plurality of cameras which themselves are positioned in a plurality of monitoring locations.

The method may comprise, providing an encoding algorithm for use by a controller of the at least one beacon to provide an encoded light sequence that changes over time. The method may also comprise using said encoding algorithm when decoding the light sequence from the beacon to identify the beacon. The algorithm is a function of a unique identification key and a sequential-based and/or time-based input.

The method may further include assigning a unique identification key to each beacon; encoding the identification key in the encoded light sequence; and providing a computer readable data store of beacon identification keys.

It may be appreciated that embodiments of the invention may provide a monitoring system which can automatically identify known users entering and passing through the monitoring zone. Embodiments can operate in a fully automated environment without the need for human input since the beacon and video analytics system of embodiments advantageously provide a machine-to-machine verification/identification approach.

At least some embodiments may provide a real time monitoring system and/or method.

Whilst the invention has been described above, it extends to any inventive combination of the features set out above or in the following description or drawings.

BRIEF DESCRIPTION OF THE DRAWINGS

Embodiments of the invention may be performed in various ways, and embodiments thereof will now be described by way of example only, reference being made to the accompanying drawings, in which.

DETAILED DESCRIPTION

Figure 1:
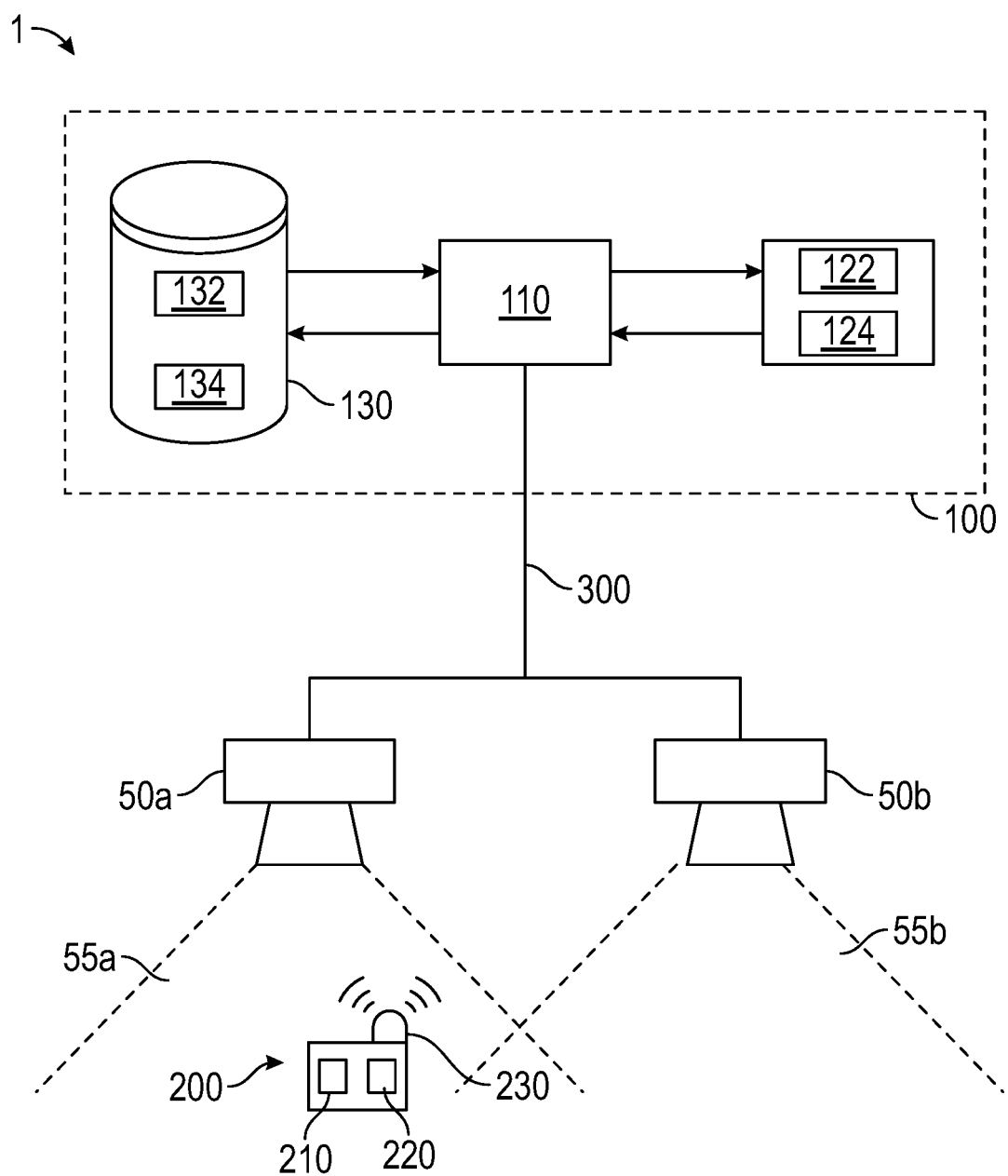
FIG. 1 is a schematic representation of a video system for use in embodiments of the invention.

A video surveillance system 1, suitable for use in embodiments of the invention is shown in FIG. 1. It may be noted that such a video surveillance system is also disclosed in our co-pending patent application GB1916245.2 (filed 8 Nov. 2019) but for completeness the system will be described in full below.

The system comprises a video analytics system 100, a plurality of video cameras 50, connected to the video analytics system 100 via a network 300 (which could, for example, include the Internet), and at least one beacon 200. In the illustrated embodiment, two cameras 50a and 50b are provided with each capturing video covering a related surveillance field 55a and 55b. The video data is transmitted over the network 300 which could be a wired or wireless network and may be local or cloud based.

The, or each, camera 50 may be sensitive to light at infrared wavelengths. Security cameras which are optimised for sensing Infrared radiation are commercially available (and may typically be used in prior art systems, with an infrared spectrum spotlight illuminating the scene with "black" light, which though invisible to the human eye can be detected by the specifically attuned sensor in the camera). Infrared video cameras may be tailored to be sensitive to a specific region of the infrared spectrum. For example, Infrared cameras sensitive to 850 nm range wavelengths are particularly common.

The video analytics system 100, comprises a processor 110, in communication with a data store 130 and a storage medium 120. It will be appreciated that the video analytics system 100 could be a network connected computer. The analytics system could be in communication with a plurality of separate camera systems and separate networks (with network comprising one or more cameras). It will be appreciated that, for example, a single networked video analytics system could be provided (for example, at a service provider) to operate a plurality of distinct surveillance systems (for example, each at separate client locations). As networked video surveillance systems are now relatively well established, it will be appreciated that embodiments of the invention could be implemented by taking advantage of existing systems with relatively simple modification and/or minimal hardware changes required.

The storage medium 120 may contain executable instructions 122, 124 for the processor 110. The storage may, for example, include random access memory (RAM) or read only access memory (ROM) and may be any convenient electronic, magnetic optical or other physical storage device.

The data store 130 may, for example, include locally stored data files, databases, websites, FTP servers and the like. As will be explained further below, the data store may be used to keep records relating to the system for use by the processor 110, such as access rules and beacon identities.

The beacon 200, may typically be a wearable device such as an identification badge or insignia. The beacon 200 may include a power source 210 such as a battery. A controller 220 is included, to control the beacons signal through light emitting element such as at least one LED 230. The controller 220 may for example, be an integrated circuit. The controller may include an input, which could, for example, be a wireless connection such as Bluetooth or Wi-Fi, to enable the initial configuration and/or set-up of the beacon.

The light emitting element 230 may be selected depending upon the properties of the light for which the camera(s) 50 are attuned. As explained further below, the controller 220 will generally cause the LED 230 to flash or pulse. By using an infrared LED the pulsing of the LED is generally of very low observability to the human eye. Infrared LEDs are increasingly compact and powerful (due to Haitz's Law), enabling easy integration into a beacon, which itself will thus be relatively compact and therefore wearable. The Infrared LEDs of the type used, for example, in "black light" spotlights for CCTV equipment, radiate large volumes of light in the Infrared range distributed around 850 nm. In operation, they generally also produce a very dull red glow that is barely visible to the human eye and only at close range. As such, whilst a pulsing LED 230, used in an embodiment of the invention, would be barely visible, it is unlikely to remain completely invisible to an observant subject. A user may find such a visible emission distracting. As such, in some embodiments, the beacon 200 may further comprise at least one masking LED at the same wavelength of the human observable red glow emitted by the infrared LED 230. Such a masking LED would provide a means to hide the pulsing Infrared light emitted from the infrared LED 230 from human observation. A further advantage of including a masking LED would be that it could provide visual confirmation that the wearable is operational and its current state (for example, low on battery power, communicating through a wireless signal, recharging the battery and so forth).

Alternatively, some embodiments of the beacon 200 could employ Infrared LED's transmitting data in the 920 nm range. Such LEDS are completely invisible to the human eye but suffer from the disadvantage that video cameras that are optimised to receive signals at this wavelength are less readily available than their 850 nm counterparts. Further, 920 nm LED's, having a longer wavelength have less energy than those at 850 nm. As such, 920 nm range LEDs generally provide less illumination to act as a beacon.

Advantageously, modern Infrared LEDs are typically visible in daylight to a distance of 30 m, even in full sunlight. Further the use of multiple LED's can provide pulsing illumination in parallel and thereby increase the operational visibility and range of embodiments of the system. In some embodiments it may be desirable for the controller 220 to adjust the brightness of the emissions from the light source 230. For example, the beacon 200 may further comprise a light sensor to allow ambient light information to be provided to the controller. Such an arrangement may enable the brightness of the LED's to be maximised in well-lit situations (to increase range) but avoid LED acting as a source of scene flooding, when light is low (which may otherwise reduce the ability of the system to isolate the beacon signals).

The emission pattern of the LED(s) 230 is governed by the controller 220 and varies over time to provide an encoded signal which can provide an identification of the beacon. For example, the LED(s) 230 can be commanded to emit a signal such as a simple series of on/off saw tooth switches over a time series. Personnel of one category could have one set of signals encoded in the lights on/off pattern whilst others would have a different pattern. It will be appreciated that brightness, duration, and many other factors could be employed to produce these different patterns. Further, if multiple LEDs are provided and controlled individually (but in a synchronised manner), then this may provide an additional level of complexity which can be encoded into the light emissions (for example each light could be treated as a separate "bit" of information). Advantageously, providing a fine-grained identification pattern that could enable the encoded signal from the beacon to identify not only a group of personnel but also a unique individual.

For the purposes of increased security, it may be preferred to provide encoded signals for the beacon which are not constant over time. This may avoid third parties observing and duplicating a signal to "clone" the identity of that beacon. Accordingly, in the system of GB1916245.2 the controller 220 may use an encoding algorithm to generate the output signal for the emitter 230. It may be appreciated that such an encoding algorithm could be similar to those used to generate one-time identification/access codes (for example for secure access to websites over the internet). Such algorithms are well established and can, for example, combine a unique identification key allocated to the beacon with a time or sequence based value, to generate an output to be used as a signal. For example, the signal may be a numerical value which is then emitted by using a particular coded sequence of pulses or flashes for each digit.

Figure 2:
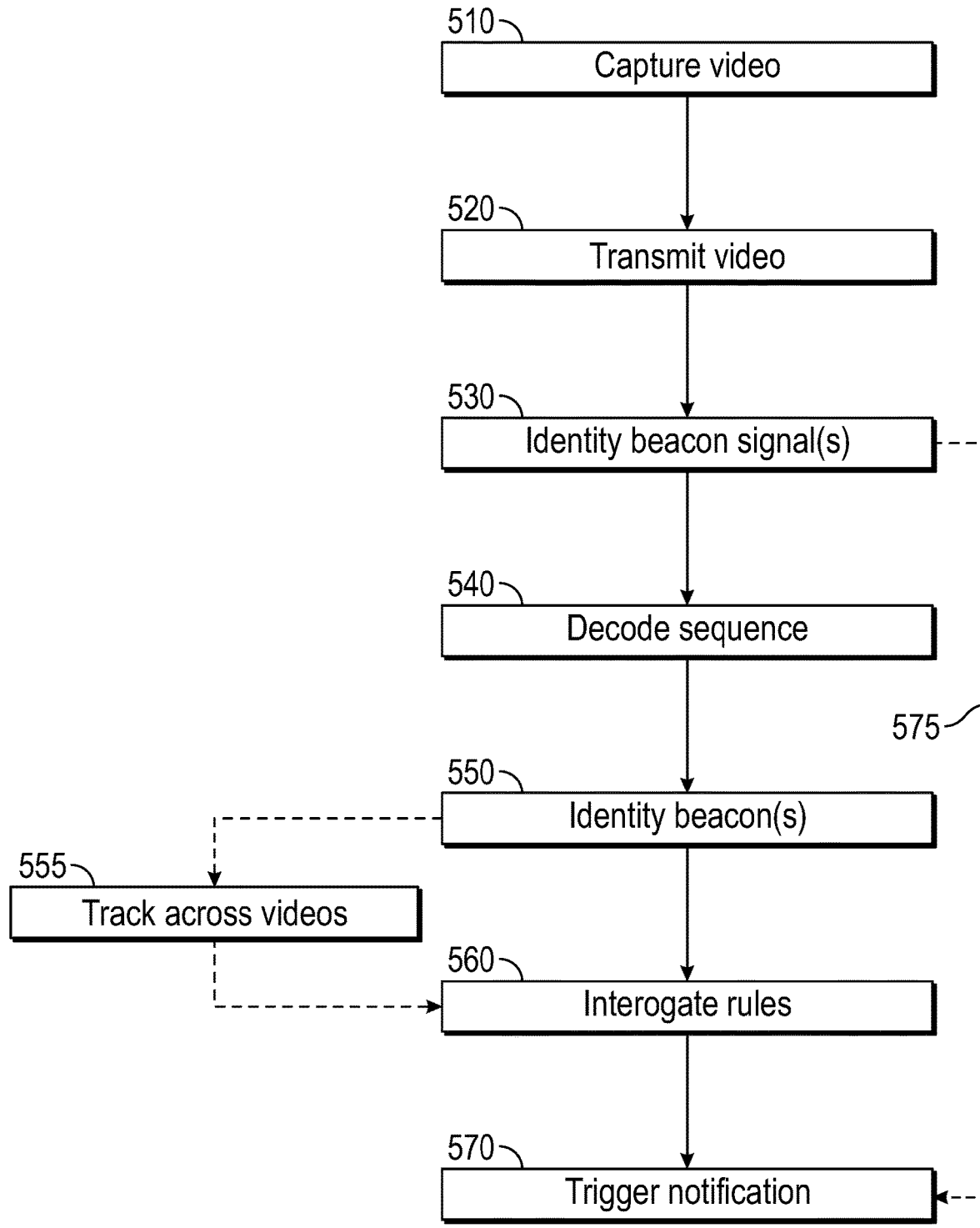
FIG. 2 is a flow chart representing the method of operation of the video system of FIG. 1.

Operation of the system of FIG. 1 will now be described further, with reference to the flow chart 500 of FIG. 2. It will be appreciated that the method may be most effective in a live system but may also work on historical/stored video data. In step 510 the camera(s) 50, monitor a surveillance area 55, capturing video data. In order to maximise the available bandwidth, the video data may be encoded to a compressed bit stream such as a video stream conforming to the H.264 format, which may then be transmitted, over network 300, to a video analysis system 100. Should the video analytics system receive the video stream in an encoded/compressed format, it is then decoded back to raw video by hardware or software by the processor 110, prior to image processing as the first step to extract useable data for machine understanding of the scene.

As represented in box 530, the processor 110 of the video analysis system 100, interrogates the video data, to identify any beacons signals from the beacons 200, that are present in the captured, transmitted, and decoded video frames. The processor 110, may for example, use a first set of process instructions 122 stored on the memory 120 to carry out the video analysis steps required to identify a beacon emission in the video frame.

Once the presence of a beacon 200 has been identified in a video stream/recording, the analysis system 100 will proceed to decode the light sequence emitted by the beacon 200. The processor 100 executes the decoding instructions 122 stored on the memory 120. The decoding instructions 122 will include the same algorithm as used by the controller 220 and will have a corresponding counter or clock synchronised with that of the controller. The decoding step 540 may for example, provide an identification key which the processor 110 can then lookup on a table 132 in the data storage 130 to provide an identification of the beacon 200 in step 550.

Once the beacon 200 is identified, the processor 110, may further look up the identity in a set of access control rules 134 stored in the data storage 130. If appropriate the analysis system 100 may then trigger a predetermined notification and/or alert in step 570. For example, an alert could be issued if a person without the required access rights enters a particular area or if a person enters an area at a non-authorised time. It should also be noted that some alerts could be triggered (as shown by line 575) in the event of a subject, for example identified by image recognition, being detected when a beacon signal has not been identified. It will be appreciated that the notifications/alerts triggered may depend upon the installation and/or user preferences such that the control rules 134 may also include a record of types of alert to be issued depending upon the situation detected. Further, the alerts may also be sent to the bearer of the wearable by sending a message to their mobile phone by SMS or a notification system or application.

In some embodiments, the identification of the beacon in step 550 may be further used to identify or track movements of the related user/objects. Such a step 555 may be used to track movement of a subject across areas monitored by multiple cameras (which may or may not be located in proximal areas). Advantageously, this may enable tracking of multiple subjects across multiple locations even in a crowded environment.

Embodiments of this disclosure provide a method to extract the beacon pulses from the background elements of the video stream. To one skilled in the art it would be understood that the computer vision algorithms described herein are merely exemplars of a plurality of algorithms that could be employed to this effect and that other algorithms in addition to those specificity described are available to achieve the same ends. In one embodiment, the security zone is observed by two cameras in close physical proximity. The first camera contains an "IR cut filter" that blocks light at the same wavelength as the beacon emits light. The second camera contains no such filter and so is sensitive to light in the beacon's IR wavelengths. Frames are derived from the two cameras, with each frame taken within a short time period relative to the other (so the frames are synchronised in time series). Pixel values from the luminance of these frames are then subtracted from each other and a luminance cut-off threshold applied to the resultant pixel difference frame. The threshold value applied can be chosen by numerous techniques known to one skilled in the art, such as mean global pixel value of the difference frame. The thresholded difference frame, will now show the location of bodies of high intensity IR pixel locations and the luminance frame can be scanned for such locations. These locations represent a 1 in the beacon encoding scheme. The absence of the beacon at a previous locus of observation represents a 0 in the encoding scheme. By capturing the 1's and 0's of the beacon over a time series, complex encoding schemes, transmitted by the beacon can be ingested by the video analytics system.

In a further embodiment a single camera captures the luminance frame without an IR cut filter. The previous frames of the time series are kept as a "running average frame" and subtracting the current frame from this running average frame and then applying a luminance threshold yields a difference frame that represents the moving foreground objects in the frame with background clutter removed. If the threshold is of a high value, then the resultant difference frame will indicate solely the location of the beacons within the frame from which the signal can be extracted in a time series by the video analytics system.

It is noted that the colour value of the IR beacon may be bright white. Thus, in a further embodiment of the system, the difference frames derived as described above, are calculated using colour values (in RGB/YUV/HSV or other format), rather than luminance pixel values. The difference frame is then filtered to only show near RGB white values, and the location of these white values are used to denote the beacon signal derived from colour frames.

It is also noted that the algorithm described above is a functional solution when employed to find a beacon signal for a single object in the scene, but this is unlikely to be applicable to all cases and scenes may be encountered in which more than one beacon is present and thus more than one encoding pulse time series will also be present. Moreover, in the observed frames, multiple moving objects carrying the beacons may cross over one another. In this case, the construction of the time series for a single beacon becomes problematic. Thus, in other embodiments, the movement of objects in the scene is tracked. One skilled in the art would know of the multiple computer vision techniques that are available to perform this function. Background foreground segmentation is often used in the first step of a tracking algorithm and these segmentation techniques split pixels into being a member of background clutter model or as a moving foreground object, based on statistical techniques such as Gaussian Mixture Modelling or Code-Book pixel look-ups. Foreground pixels are then passed into sophisticated tracking engines that combine individual pixels into single tracking objects by using connected-component labelling algorithms, in concert with hole filling algorithms (morphological operations). The individual objects are then tracked and compared to a model of expected movement to remove statistically outlying movements and the satisfactory movements recorded by the video analytics system. Yet more computationally advanced algorithms such as optical flow methods or segmentation by Convolution Neural Networks may also be used in tracking functionalities, but in sum, these techniques provide a mechanism to automatically split and track moving objects. In some embodiments of the device the encoded beacon sequence is attached to a single moving object to allow decoding the sequence on a per object basis over a time sequence and allow identification of multiple beacons in a single frame in difficult environments.

Embodiments of the invention provide a mechanism to store the data or meta-data. This data can be kept in memory and analysed on the fly by the video analytics system or placed into a database where it can be analysed at a later date. This analysis could be to derive associations amongst the data that is only visible from a prolonged time series, such as the number of times in a day that a security guard has entered an area. In another embodiments searching for and finding an incident on historical data then allows the partnered video data to be observed and interpreted by human operators.

In embodiments it is envisaged that the following data and meta data could be collected by the video analytics system. One skilled in the art would recognise that this list is not exclusive and that additional elements of data and meta data could prove useful in real-time analysis or be stored for subsequent review. Such data includes: the camera number, the pulsed flashes of the beacon, the beacon signal strength (number of pixels), the beacon centroid location (X, Y), the beacon's derived Z location (from a pinhole camera model, from a 3D camera using stereoscopy or structured light or range finding technology), the beacon's derived Z location from the separation of matching beacons on a single object and passed through a range finding algorithm, the time of the observations. In some embodiments the Meta data such as the beacon identification tag derived from a lookup table could also be stored in the database.

As noted above, the beacon 200 may typically be a wearable device. This could for example, include a badge or wrist band. However, typically the cameras of video surveillance systems are mounted high up, over the area being monitored and therefore it is advantageous to provide a beacon 200 which is located above a subject's waist. For example, in some embodiments, a beacon 200, could be incorporated into an epaulette, which are often present in the uniforms of security, police or military personnel. Epaulettes are worn on both shoulders and as such, at least one is generally visible from an orientation likely to observed by a CCTV camera in a surveillance system; as such, embodiments may take advantage of this by having beacons with synchronised signals on each epaulette (for example a connection such as a wireless Bluetooth or Wi-Fi link may be provided between the pair of epaulettes to enable such set up, or employ a time based signal, which would always be synchronised between time matched wearables). As epaulettes are close to eye level it may be desirable to provide a shield or mirror to direct light from the light emitting elements 230, in a preferred emission direction—typically away from the users face.

Figure 3:
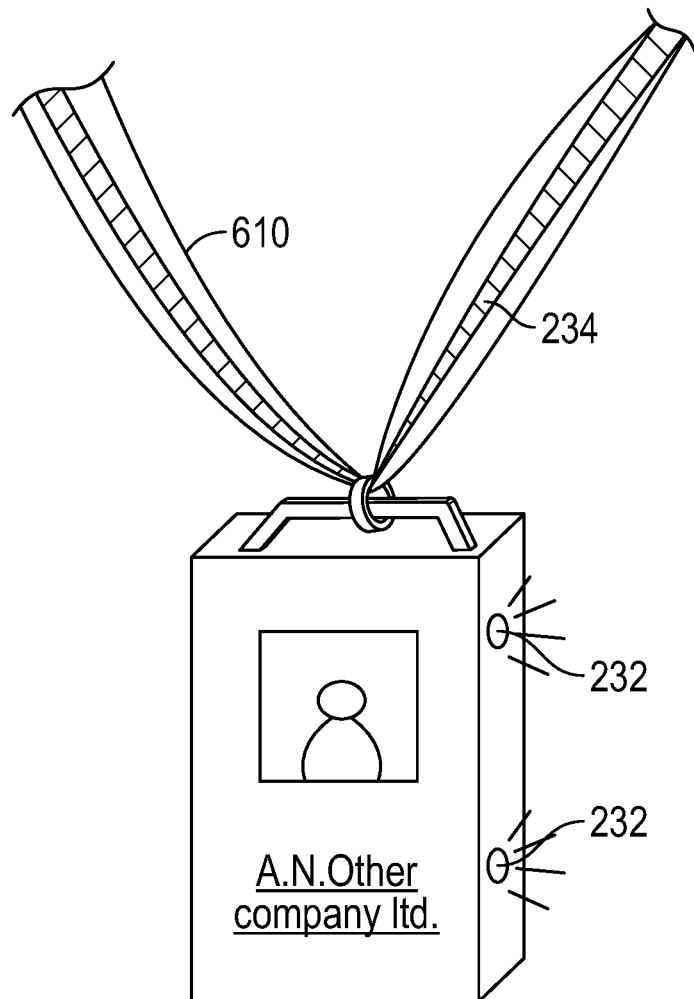
FIG. 3 is a schematic representation of an identity lanyard including a beacon for use in embodiments of the invention.

One implementation of the beacon 200 is represented in FIG. 3. In this embodiment the beacon is incorporated into a Lanyard of the type which are worn around the neck and commonly used in workplaces or at functions and events. Such lanyards generally comprise a cord or strap 610 which is worn around the neck and an identification badge 600 attached thereto. A beacon 200 for use in embodiments of the invention could be integrated into a lanyard or provided as an add-on/modification to an existing lanyard. Components such as the battery 210 and controller 220 may for example be conveniently located within the badge 600 or a holder associated with the badge.

In some embodiments the badge (or associated badge holder), 610 could be provided with one or more light emitting element(s) 232 of the beacon. In other embodiments, the light emitting element(s) 234 could be incorporated into the strap 610 of the lanyard. Such an arrangement is particularly useful as it can enable the element and signal to be visible along a greater area. For example, a transparent or translucent portion of the strap 610 may be provided with multiple distributed LEDs or with LEDs connected to a light diffusing arrangement. This may enable the light emitting element 234 to be visible from all directions including the rear. The light diffusing element could, for example, be formed using optical fibres, light pipes, or flexible light diffusing sheets. An adjacent region of the strap 610 may have a contrasting colour to the light emitting element or associated light diffuser. This may provide increased contrast for the video analysis to assist in identification of the beacon 200 and the pulsed signal.

The present disclosure further builds upon the above system and method and will be described further with reference to the flow chart of FIG. 4 and the illustration of FIG. 5. Whilst the use of an encoded binary signal from the beacon provides a high level of security the applicant has also found that identification and decoding of a constantly changing signal can be computationally burdensome.

Figure 4:
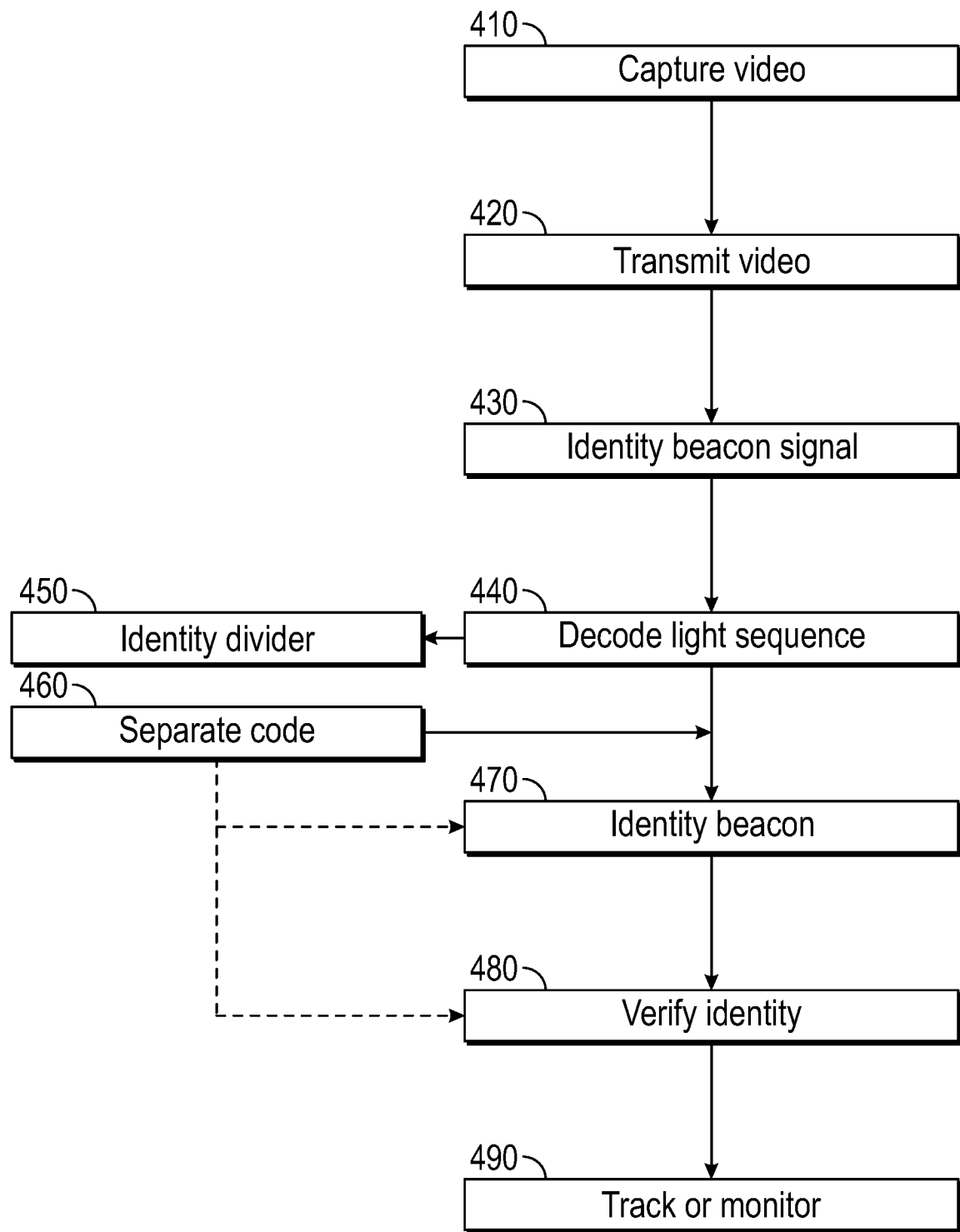
FIG. 4 is a flow chart representing a further method of operation in accordance with embodiments of the invention.
Figure 5:
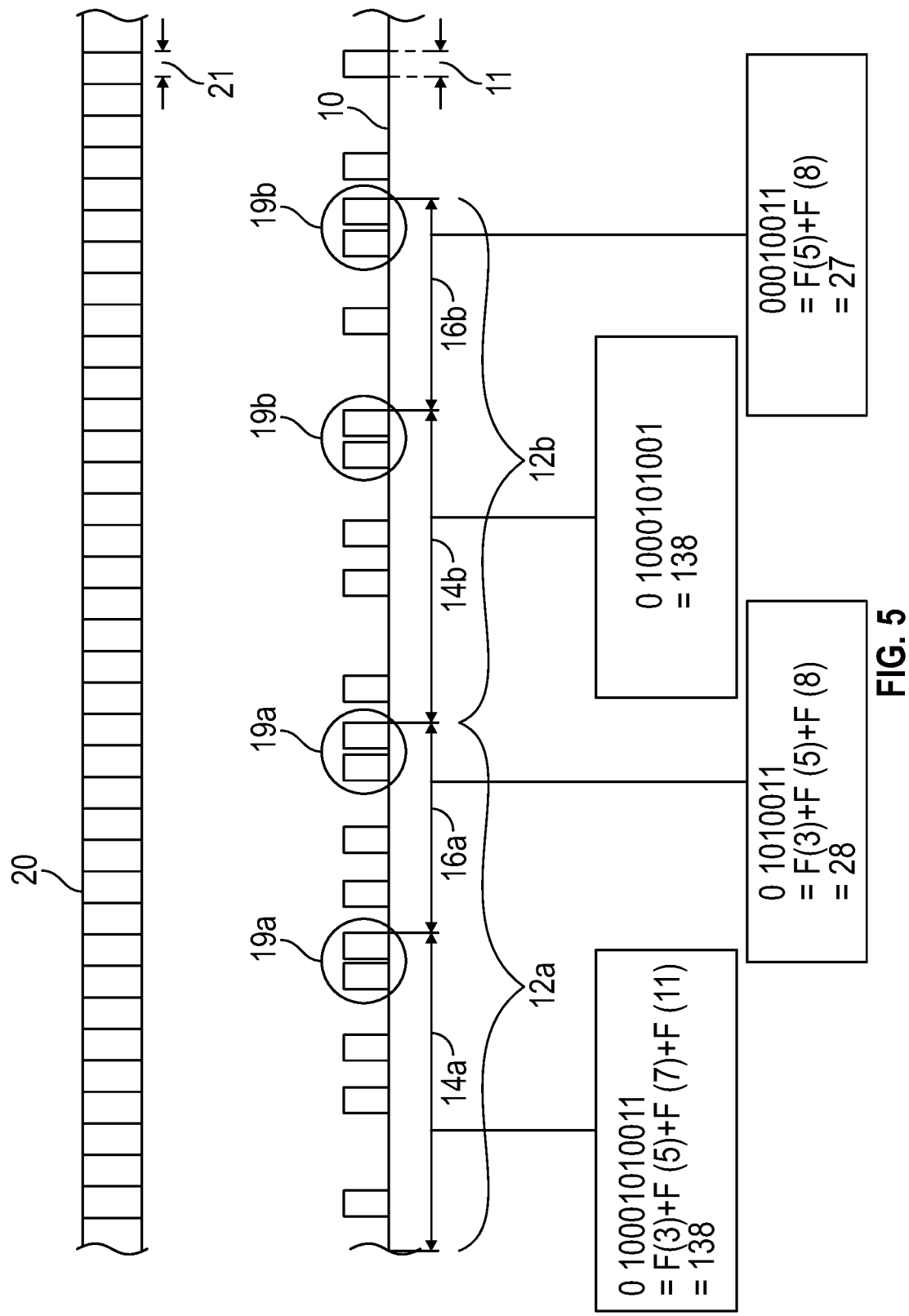
FIG. 5 schematically represent a data signalling approach for use in embodiments of the invention.

Accordingly, a modified method and system is represented in FIGS. 4 and 5 using a two-part signal.

As in the previous embodiments, the controller 220 of the beacon 200 is arranged to provide an actuation sequence to the light emitting element 230, which consists of a binary on/off signal. As represented by FIG. 5, the signal 10 consists of packets 12, each of which represents the repeated set of data that the beacon is transmitting to be identified by the camera 50 and analysis system 100. Each packet 12, comprises a fixed number of individual bits 11, each bit being a binary on/off (i.e. 1/0) corresponding to a pulsed light emitter 230. The bit rate of the signal generally matches the frame rate of the camera (as represented schematically by the sequence 20, made up of a series of frames 21 in FIG. 5) such that each bit will be captured by a frame 21 of the video 20.

Within each packet 12, the signal is divided into a plurality of sub-packets. In the embodiments detailed below, two sub packets are described, 14 and 16, however, in other examples, different and/or more numerous combinations of sub packets could be employed. Sub-packets 14, has a fixed code of bits, which repeats in each packet of the signal. This is shown by the identical bit sequences (0, 1, 0, 0, 1, 0, 1, 0, 1, 1) in both first sub-packets 14a and 14b of FIG. 5. The other sub-packet 16 may change between packets, as shown by the non-identical coding bits of the consecutive sub-packets 16a and 16b in FIG. 5. For convenience, it may be noted that the fixed sub-packet 14 is referred to herein as the "first" sub-packet and the changing sub-packet 16 is referred to as the second "sub-packet". The skilled person will of course appreciate that this does not imply an order to the sub-packets but rather serves to indicates that each sub packet is one of two parts comprising the whole packet. In the illustrated example the first sub-packet 14 comprises 12 bits of binary signal and the second sub-packet comprises 8 bits of binary signal. Thus, the total packet size is, in this example, 20 bits. As will be discussed further below the bit length of the packet and the sub-packets may be selected depending on overall requirements of the system.

To assist the video analysis system in distinguishing between consecutive packets 12a, 12b and between the sub-packets 14, 16 the signal 10 can include codes within the bits that serve as a divider. The divider 19a, 19b is a repeated sequence of bits which cannot present elsewhere in the signal. In the illustrated example the divider signal is a pair of 1 bits (i.e. two consecutive pulses of light emitted by the beacon). As will be explained further below, a particularly convenient approach is to encode the signal 10 using Fibonacci coding, since Fibonacci coding represents integer numbers using code words based upon the Fibonacci numbers with each code word always ending with "1, 1" and no other instances of "1, 1" being present in the code word.

The purpose and operation of the sub-packets 14 and 16 will now be further explained with reference to the flow chart of FIG. 4. As with the previous embodiment, the video system operates to capture a stream of video data in the first step 410 using the camera(s) 50. The captured data is transmitted to the video analytics system 100, for example over a network 300 in step 420. Upon receiving a video stream 20, the analysis system first seeks to identify any beacon signals present in step 430. The repeating nature of the first sub-packet 14 of the signal 10, simplifies the computational task for detecting the signal for the video analytics system 100, providing a repeating anchor into the signal. Thus, the video analytics system 100 can decode the flashing sequence detected in the video data back into a binary signal stream in step 440.

When decoding the light sequence, the video analytics system 100 can analyse the signal to find divider signals 19 in step 450. Identification of the divider signals enables the signal captured in the video data to be parsed into individual packets and sub-packets in step 460.

The repeating sub-packets 14 may then be used to identify the beacon as shown in step 470. As shown in the example of FIG. 5, where the binary signal is using Fibonacci coding, the binary sequence of the fixed portion can be identified as a series bits which may be in the state 1 or 0 and ending at the divider signal (i.e., a 1, 1 signal). Each of the individual bits (other than the final appended "1") correspond to the position of a Fibonacci number which can be summed to arrive at the encoded integer number. Thus, the example sequence of FIG. 5 (0, 1, 0, 0, 0, 1, 0, 1, 0, 0, 1, 1) can be corresponded to the Fibonacci numbers F(3)+F(7)+F(9)+F(11) providing a value of 138. This integer is the ID of the beacon transmitting the signal 10. This sequence and ID is repeated in every one of the fixed sub-packets 14 (as shown for example by sub-packets 14a and 14b) in the signal and is a unique value allocated to a specific beacon 200.

Alongside identification of the beacon ID the separating step of 460 also enables the video analytics system to separate out the second sub-packet 16 and decode its binary sequence which may be different from one packet 12a to the next 12b. For example in the illustration one second sub-packet 16a can be seen to correspond to the bits 0, 1, 0, 1, 0, 0, 1, 1 and the next second sub-packet 16b can be seen to correspond to the bits 0, 0, 0, 1, 0, 0, 1, 1. Thus sub-packet 16a is decoded as Fibonacci numbers F(3)+F(5)+F(8) returning an integer value of 28 and sub-packet 16b is decoded as Fibonacci numbers F(5)+F(8) returning an integer value of 26.

The value of the sub-packet 16 is used by the system as a code word and used to verify the beacon identity in step 480. For example, the integer value from the sub-packet 16 of a single packet 12 or the sequence of integer values over several packets 12a, 12b can be used in a checksum. For example, using a public-private key which is shared between the beacon and the video analytics system or using a time-based encoding where the time is shared by both the beacon and the video analytics systems decoding the bits.

Having identified the beacon 200 and verified its authenticity the system may, in step 490, track or monitor the beacon; for example recording a log of its movements within the monitored area or confirming the access rights of the bearer into the monitored area.

The example above uses a 20-bit packet length and with the bit rate approximately matched to the camera frame rate for a typical current IP camera (25 Frames Per Second), this would allow an entire packet to be transmitted/received in less than 1 second. It may be appreciated that the packet length is a trade-off between the amount of data included, in comparison to the time to achieve an initial resolution of the identifier packet and also the reliability of the resolved tracking/identification object. As such, embodiments of the invention may allow the packet lengths to be selected during configuration—for example allowing a shorter packet where fewer subjects are required and thus allowing a quicker resolution of each identification.

Likewise, the size of the sub-packets may be configurable such that the same basic system could be used for a variety of applications. For example, if a system were being used in a high security environment the total number of identifiable beacons could be reduced (reducing the ID sub packet 14), to allow a greater number of bits to be available to describe the codeword portion (the security sub-packet 16 is longer)

of the packet. On the other hand, a surveillance or monitoring system used purely for collating commercial Real Time Location data (for example tracking the movement of shopping trolleys through an area) may benefit from the availability of a high number of beacon IDs but require only a very basic verification function from the code word. In such a situation, the ID sub-packet 14 would be maximised and the codeword sub-packet 16 minimised.

An additional parameter, that may provide useful configurability to methods and systems of embodiments, is whether the security code word is verified over a single or multiple (typically sequential) packets. Verification over multiple packets can greatly increase the security even when using a short code-word, since the individual codes are collated over a time period the probability that the entire time series is correct is the probability of each sub-packet being correct to the power of the number of packets collated. The probability of being able to spoof this ever-changing signal by chance alone, gets very small, very quickly. It will, however, be appreciated that verification on a single packet basis is less likely to impacted by signal interference or other environmental factors corrupting the reception of the code word.

For a fully reliable and passive/automated system the camera 50 and video analytics system 100 are not synchronised with the beacons 200. This can result in the risk of misalignment between the switching of the light emissions and the frames of the video capture causing errors, in the reading the state of the beacon, by the video analytics system. This issue is particularly notable when the video frame rate and signal bit rate are matched (which is desirable for the purpose of maximising the data capture and thus speed of identification/tracking). This is schematically illustrated in FIGS. 6A and 6B (and it will be appreciated that the diagrams of FIG. 6 are purely for understanding purposes and are not intended to be in any way to scale).

Figure 6A:
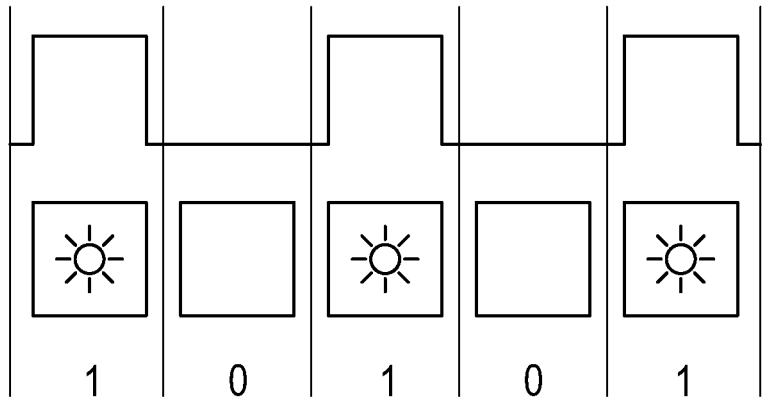
FIGS. 6A to 6C are illustrative diagrams representing the timing and phase issues between an unsynchronised video capture and binary data signal source.

In FIG. 6A the binary signal 10 and video frames 20 are approximately in phase and each bit 11 of the signal 20 is mapping onto a single frame 21 of the video stream. As shown by the beacon light 230. This results in a correct reading of the signal when the video is analysed as shown by the resulting binary output 1, 0, 1, 0, 1.

Figure 6B:
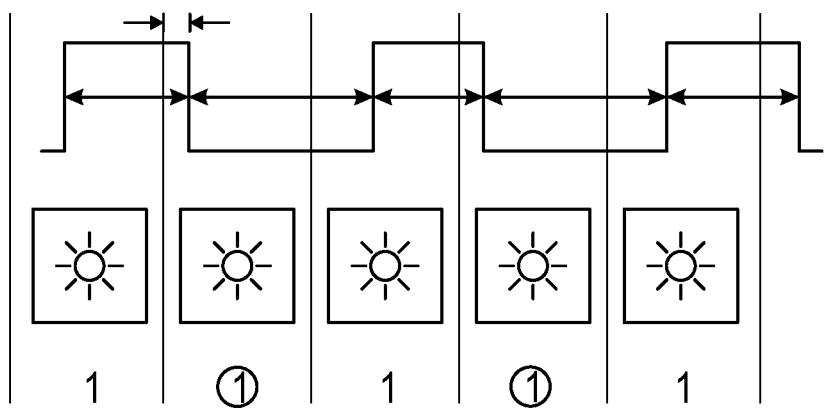

In FIG. 6B the signal 10 and video are out-of-phase (as indicated by the time difference T) such that the switching on/off of the beacon light element 230 changes whilst the shutter of the camera 50 is open. This results in the on/off signal straddling consecutive frames of the video feed. As a result, rather than seeing a clean on/off from the beacon 230 the frames record an "on" signal. Whilst this signal may be of reduced brightness, in a real world/noisy environment it may not be possible to distinguish such a difference. As a result, when the video Is analysed, the resulting binary output returned may (in this example) be 1, 1, 1, 1, 1. Thus two additional "1" are returned which should have been registered as "0". Further, when operating continuously, both the duration of each pulse and the frame rate of the video are constant and, therefore, the phase difference T between the signal and frames will remain indefinitely.

The applicant has now recognised that this problem can be overcome without the need to adjust the video frame rate or substantially change the data transmission of the signal. Thus, in some embodiments the system is configured such that the controller of the beacon includes a prescribed amount of jitter into the timing of the signal 10. It will be appreciated that jitter is the deviation of the signal from true periodicity. Whilst all signals may include some element of jitter this would normally be negligible in a controlled on/off switching sequence such as that in systems of the invention. In embodiments of the invention a small, but non-negligible, quantity of jitter is intentionally introduced to the signal. For example, the jitter introduced into the signal may be less than 1% (for example less than 0.5%) of the switching time of the signal. Thus, for a typical camera frame rate of 25 FPS each pulse of the signal may be 40 milliseconds and a jitter of around 100 microseconds could be introduced. Thus, the pulse rate of the signal 10 with the introduced jitter will be 40 milliseconds+/−100 microseconds.

Figure 6C:
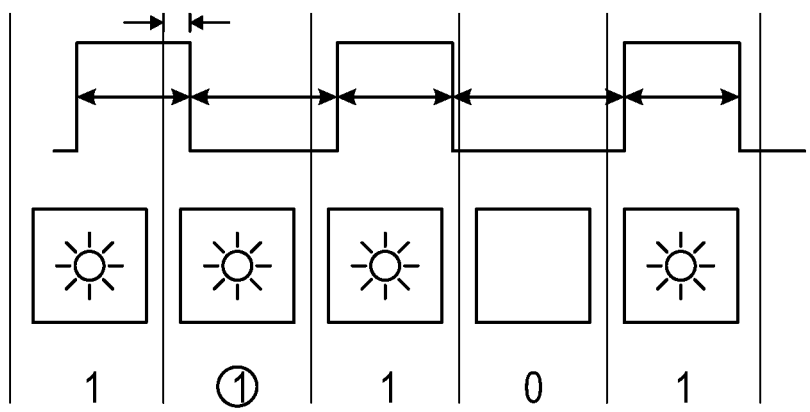

The effect of such jitter is illustrated (with some exaggeration for ease of understanding) in FIG. 6C. In this example the initial out of phase timing T' is the same as that of FIG. 6B. The introduced jitter causes the duration d' of each pulses of the signal 10 to vary slightly in duration (as the signal is deviating from true periodicity). This small difference means that the phase relationship between the video frames 20 and the signal 10 is not fixed but rather shifts in phase over time. As may be noted in the figure, this drifting of phase alignment can ensure that even when a signal is initially out of phase (causing the second frame to be misread as "1" rather than "0") it is able to drift back out of this misalignment to a sufficient extent that subsequent frames are not misread. This same effect can be achieved by adding a non-fixed temporal value to the beacon pulse emission rate, for example a random value between 0 and 100 milliseconds.

Whilst the embodiments above have been described in the context of a general video analysis system having many potential uses, the applicant has now also identified a specific application of the methods and systems described herein, which lies in the area of computer assisted monitoring of exposure to hazardous materials or situations. In particular, such applications may benefit from the distanced, contact free, autonomous working of the methods and systems described herein, to provide such monitoring without encumbrance to the subjects monitored. This may, for example, be particularly useful for medical or care staff working in areas where they risk exposure to infectious diseases (such as Covid-19/SAR-CoV-2). Advantageously, a system in accordance with such an embodiment could be implemented using a conventional CCTV camera (or even a camera already in-situ), by providing subjects being monitored with a simple wearable beacon as described, which unobtrusively transmits a signal, substantially invisible to the wearer or the patients that they are providing care to.

Figure 7:
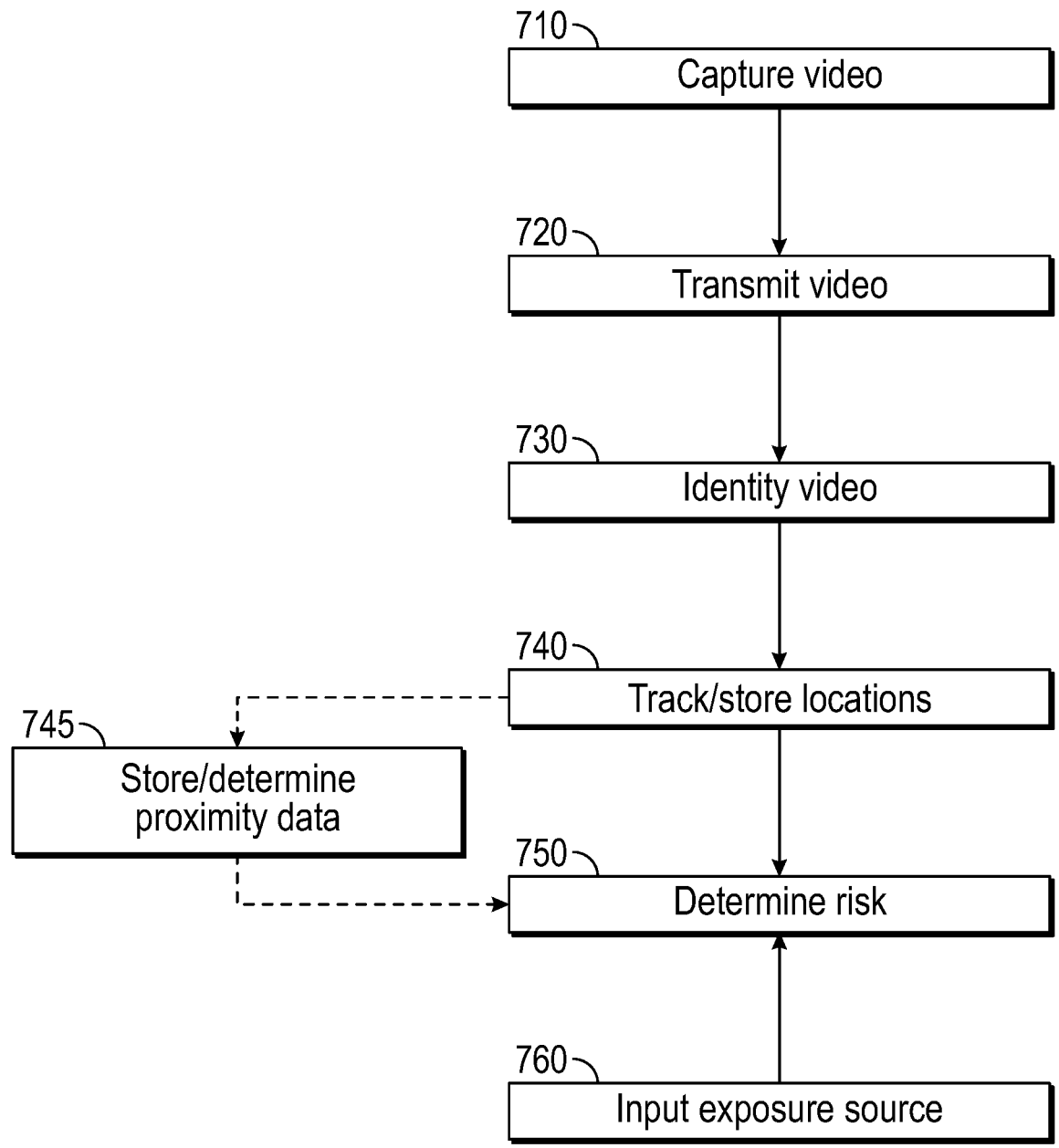
FIG. 7 is a flow chart representing methods and systems in accordance with embodiments for risk monitoring.

In some embodiments, the system or methods described herein may be utilised to provide a risk monitoring system, by tracking the locations of beacons. Such a system and method is illustrated by the flow chart presented in FIG. 7. In a similar manner to other embodiments described herein, a data stream of video is first captured in step 710. The video data is then transmitted to a video analysis system in step 720 and in step 730 the identity of beacons present within the monitored area are identified (using any of the methods described above). The video analytics system may then track and store the locations of each beacon in step 740. Typically, a location history for each beacon may be built up over a period of time. Optionally, the analytics system may also, in step 745, determine and store proximity data for each identified beacon. The proximity data may be based upon the proximity of the beacon to specific points within the monitoring field and/or to any other beacons that are detected Based upon the monitored information, the system and method of this embodiment may determine an exposure risk for each beacon and by extension, the bearer of that beacon, as shown in step 750. For example, the exposure risk may be a function of the distance between the beacon and a potential risk and/or the duration that the beacon was within a specified proximity to that risk. It will be appreciated that the exact formula or parameters used to quantify the exposure risk will be dependent upon the specific application of the system. However, the 2020 COVID pandemic has provided the scientific community with motivation to provide comprehensive theoretical models that describe the relationships between the factors described above (for example M. Kriegel et al 2020). The system described herein has the unique property of capturing the experimental, "real world", data that these theoretical models describe and thus can provide an observed dataset to test these models against. The utility of being able to test the accuracy of the theoretical model is extremely useful in understanding the mechanics of infection and to therefore propose methods of infection control.

Typically, the exposure source used in the method or system of this embodiment may either be designated by its own beacon or may be defined as a fixed point/area in, or defined relative to, the monitoring area. In some embodiments it step 760 of inputting or defining an exposure source may be possible at any stage. For example, the input of a new or updated source in step 760 may result in an updated risk exposure being determined in step 750. This could for example be useful in cases of infectious diseases where it may become apparent retrospectively that one of the subjects has been infected (and therefore the input at 760 could be an action to designate the relevant beacon ID as an exposure source).

Systems and methods of the invention may also be used to monitor other forms of exposure. For example, if the location of one or more pieces of equipment is either known or allocated a beacon the proximity and/or duration of exposure of beacons entering the area could be determined, recorded, and aggregated. This could for example be useful in monitoring the exposure to a source of radiation such as an x-ray apparatus. Likewise this could be useful in determining decibel exposure in working or leisure environments.

Although embodiments of the invention have been described above with reference to preferred embodiments, it will be appreciated that various changes or modification may be made without departing from the scope of the invention as defined in the appended claims.

For example, in some embodiments a beacon or beacons used on a subject may be used for additional image processing uses. For example if a beacon or beacons are provided which are a fixed or known distance apart on a subject it would be possible to measure this distance and thus generate the depth location (Z plane location) of the beacons when processing the 2D frames of captured video.

Further, in order to decrease the computational requirements for processing signals in real-world environments it may be desirable to take steps to clean up the video feed either at the camera or as it is provided to the video analysis system. Accordingly, in some embodiments, the camera(s) used for video capture may be effectively modified to operate as sensors for the beacons, by reducing the volume of light that arrives at the sensor. For example, when the beacons use Infrared LEDs as their light source, the volume of light that these sources produce is so substantial that this will invariably be regarded by the light sensor in the camera as a very high luminance value (for example 255 in an 8-byte greyscale image). Thus, in some embodiments the incoming light could be filtered by a device such as darkened glass, to reduce the overall quantity of light being captured by the sensor on the camera, without changing the value of the pixels relating to the beacon LEDs which are still saturating the sensor capacity to register light at those pixels. Thus, adding darker filters can suppress the albedo light reflected from the materials of the background environment, whist the saturated pixels from the point source IR LED remain brilliant white. In this way, it is possible to run a threshold filter across the frame to isolate only those pixels above a threshold luminary value and thus isolate only the IR pulsing LED's, thus deriving the signal in an extremely computational efficient method, in which the signal is very clean and unpolluted by background noise. In such an implementation the cameras could be installed in paired arrangements to capture parallel video streams. One of each paired cameras would act as a sensor providing clean, error free, machine-readable data and the second camera would act as image capture device to provide human readable data (normal CCTV output) and for both data from both cameras to be stored for analysis and recall side by side.

In further embodiments of the system the same effect of reducing the volume of light entering the camera can be achieved by increasing the shutter speed of the camera whilst dampening the gain electronically applied by the camera to the captured frame. Since the point LEDs are producing more light than the surrounding albedo reflected light from the background environment, the LEDs will saturate the sensor to produce a white pixel at its location, whilst the rest of the reflected light produced by the environment will be abrogated and will produce less luminance as less light is reflected in the same time window. This arrangement has the additional advantage of being electronically controlled and does not require additional devices to add to the CCTV camera. Further, this method also reduces the window in time in which the image is captured and thus reduces the probability that a bit in the data packet 20 may be misaligned due to it being on a border between two captured frames as described above.

The invention claimed is:

1. An exposure monitoring system comprising:
at least one camera to observe a monitoring area;
a plurality of beacons each comprising at least one light emitting element and a controller to provide an actuation sequence to the light emitting element; and
a video analytics system comprising a processor configured to receive video data captured by the at least one camera,
analyse the video data for a presence of light emissions from the beacons,
decode the actuation sequence of the light emissions from any detected beacon to provide an identification for the beacon,
compile a location history for each beacon detected within the monitoring area, and
determine an exposure risk associated with each beacon.

2. The exposure monitoring system of claim 1 wherein the processor is configured to use the location history of each beacon to determine proximity to at least one exposure source, said proximity being used in calculating the exposure risk.

3. The exposure monitoring system of claim 2, wherein the processor determines the proximity with respect to time.

4. The exposure monitoring system of claim 2, wherein the exposure source is a fixed point defined within or relative to the monitoring area.

5. The exposure monitoring system of claim 2, wherein the exposure source is at least one of the plurality of beacons.

6. The exposure monitoring system of claim 5, wherein the processor determines a potential relative exposure risk for each beacon detected within the monitoring area relative to any other beacons detected within the monitoring area.

7. The exposure monitoring system of claim 6, wherein the video analytics system has an input for flagging a specific beacon identification as an exposure source and wherein in response to a new input the processor uses the potential relative exposure to determine a revised exposure risk for each beacon.

8. The exposure monitoring system of claim 1, wherein at least some beacons are a wearable device.

9. The exposure monitoring system of claim 1, wherein the light emitting element emits infrared spectrum light.

10. The exposure monitoring system of claim 1, wherein the processor comprises a machine-readable storage comprising a database of unique identification keys for a plurality of beacons.

11. The exposure monitoring system of claim 1, wherein the controller uses an encoding algorithm to provide a non-repeating actuation sequence and the processor uses the encoding algorithm in identifying the beacon.

12. The exposure monitoring system of claim 1, wherein the data collected by the exposure monitoring system is fed into a theoretical mathematical models of transmissibility, to validate an efficacy of these models.

13. The exposure monitoring system of claim 1, wherein a subject or location exceeding a threshold value of risk leads to a generation of a notification which is transmitted to the subject of the risk or the subject responsible for managing the location.

14. A method of monitoring exposure, the method comprising:
providing at least one camera to capture video of a surveillance field;
providing at least one subject within the surveillance field with a beacon to transmit an encoded light sequence;
analysing video from the at least one camera to:
detect the beacon output within the surveillance field,
decode the light sequence from the beacon to identify the beacon,
track a location of the beacon over time, and
determine an exposure risk to the subject based upon the location of the beacon over time.

15. The method of monitoring exposure of claim 14, wherein determining the exposure risk comprises determining a proximity, and associated duration, of the subject to an exposure source.

16. The method of monitoring exposure of claim 15, wherein the exposure source is identified by a beacon.

17. The method of monitoring exposure of claim 16, wherein the method further comprises flagging at least one subject with a beacon as an exposure source.

18. The method of monitoring of claim 14, further comprising determining and storing a relative proximity over time when multiple beacons are identified within the surveillance field.

* * * * *